United States Patent [19]

Harbolt et al.

[11] Patent Number: 4,710,360

[45] Date of Patent: Dec. 1, 1987

[54] APPARATUS FOR DISSOLVING UREA AND OTHER ENDOTHERMIC MATERIALS

[75] Inventors: Bruce Harbolt, Northridge; Perry L. Murata, Torrance; Neal C. Burmaster, Anaheim, all of Calif.

[73] Assignee: Union Oil Company of California, Los Angeles, Calif.

[21] Appl. No.: 872,807

[22] Filed: Jun. 11, 1986

Related U.S. Application Data

[62] Division of Ser. No. 668,036, Nov. 5, 1984, Pat. No. 4,610,714.

[51] Int. Cl.⁴ .............................................. B01D 11/02
[52] U.S. Cl. .................... 422/269; 422/281; 422/286; 414/354; 414/371
[58] Field of Search ............... 422/261, 268, 269, 281, 422/285, 286, 273; 264/14; 71/64.06; 414/354, 371

[56] References Cited

U.S. PATENT DOCUMENTS

| | | | |
|---|---|---|---|
| 300,719 | 6/1884 | Mitchell | 414/354 |
| 360,996 | 4/1887 | Büttner | 422/281 |
| 2,155,854 | 4/1939 | Barnes et al. | 422/281 |
| 3,062,626 | 11/1962 | Beck | 422/281 |
| 3,210,154 | 10/1965 | Klein et al. | 71/64.06 |
| 3,836,611 | 9/1974 | Mavrovic | 264/14 |
| 4,390,506 | 6/1983 | Schumacher | 422/281 |
| 4,449,900 | 5/1984 | Lerner | 71/64.06 |

FOREIGN PATENT DOCUMENTS 1266874  3/1972  United Kingdom ................. 264/14

*Primary Examiner*—David L. Lacey
*Attorney, Agent, or Firm*—Dean Sandford; Gregory F. Wirzbicki; Robert A. Franks

[57] ABSTRACT

Apparatus for endothermic dissolutions in water, including: a mixing tank 40, wherein solute is slurried with water; pump 59 and spray pipe 63, for spraying slurry into spray box 70; and fan 75 for drawing ambient air upwardly, in direct heat exchange relationship with descending slurry droplets. Dissolution is promoted, as the droplets extract heat from the countercurrent flow of air.

9 Claims, 1 Drawing Figure

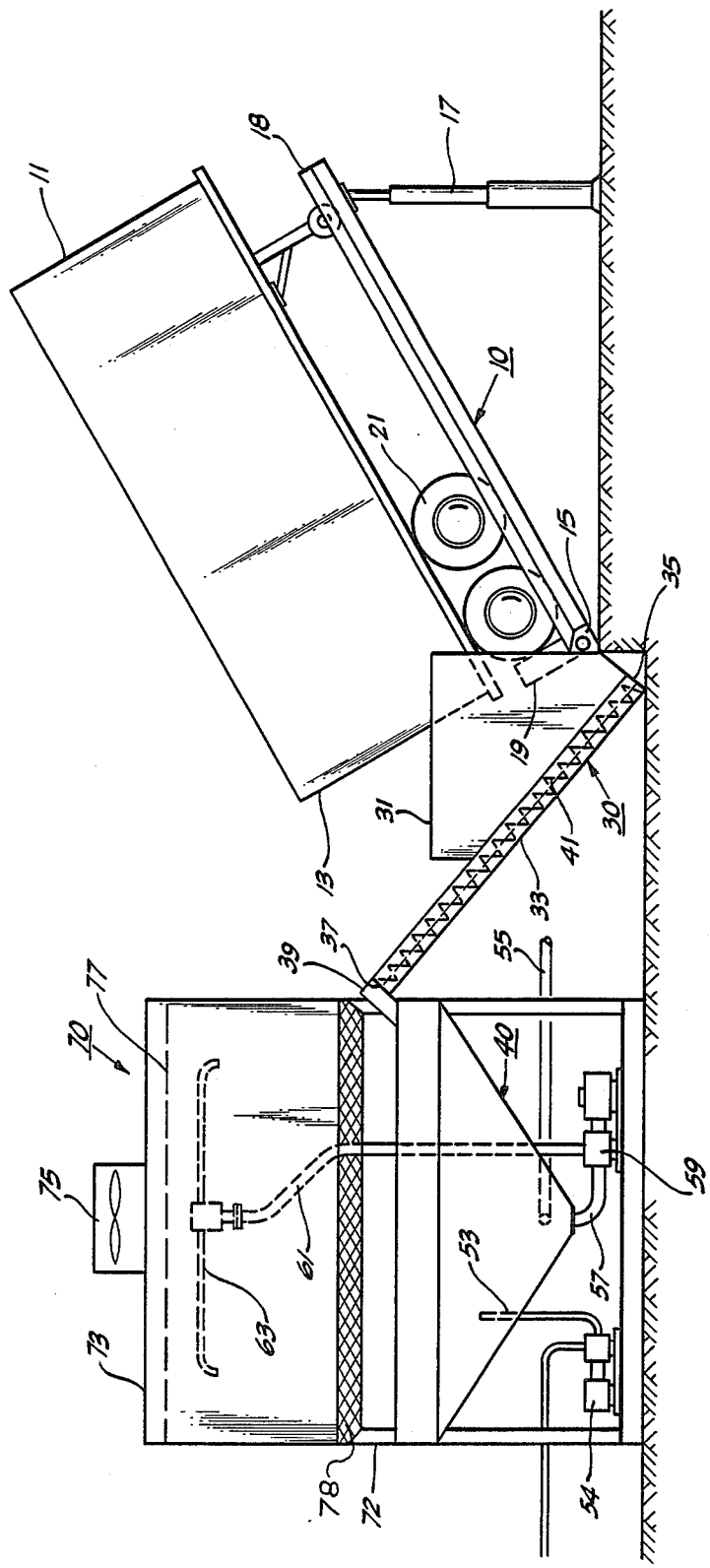

APPARATUS FOR DISSOLVING UREA AND OTHER ENDOTHERMIC MATERIALS

This application is a division of application Ser. No. 668,036, filed Nov. 5, 1984 and now U.S. Pat. No. 4,610,714.

BACKGROUND OF THE INVENTION

1. Field of the Invention

This invention relates to an apparatus and method for dissolving endothermic materials, without the use of fossil-fuel derived heat. This invention is especially suitable for dissolving agricultural chemicals such as urea, potassium chloride, ammonium nitrate, etc.

2. Description of the Art

Commercial plants for dissolving endothermic materials such as urea and potassium chloride generally require fossil fuel-derived heat for efficient operation. This is due to the negative heat of solution for endothermic materials such as solid urea. (The negative heat of solution for urea is approximately 109 BTUs per pound.) Thus, in the conventional fossil fuel-fired plant, hot water or steam and water at a temperature of approximately 180° F., are mixed with urea to produce a solution having a temperature of about 90° F. and 19 to 23 percent nitrogen. Unless adequate heat is supplied, this mixture becomes cold and rapidly approaches the crystallization temperature. Moreover the rate of dissolving is retarded and the production capacity is very low in the absence of sufficient heat.

It will be appreciated that it would be desirable to operate without fossil fuel-derived heat if such an operation could be economically carried out. Moreover, the elimination of fossil fuel from a process for dissolving endothermic material would be beneficial from the standpoint of conserving resources and, in addition, the pollution problems inherent in fossil fuel-derived heat would be avoided.

Thus it is one object of this invention to provide an energy efficient and economical method for dissolving endothermic materials without the use of fossil fuel-derived heat.

It is another object of the invention to provide a method and apparatus for dissolving endothermic materials which method and apparatus relies on natural environmental conditions, i.e. the weather.

It is another object of the invention to provide a process for dissolving endothermic materials which relies on the heat obtained from ambient air and thus it is particularly useful in locations wherein the average temperature of the ambient air is high, for example Hawaii.

Moreover, it is another object of this invention to take advantage of the temperature and humidity of the ambient air found in various locations to provide heat to a process for dissolving an endothermic material.

Finally, it is an object of the instant invention to provide a method and apparatus to prepare high concentrations of urea in water, for example 19 to 23 percent, by weight, nitrogen solutions, without the danger of crystallizing urea from such aqueous solutions and without the use of fossil fuel-derived heat.

Further objects and advantages are to provide improved steps, elements and arrangements thereof in a process effective in accomplishing the intended purposes.

Other objects and advantages of the instant invention will become apparent from a careful reading of the specification below.

SUMMARY OF THE INVENTION

This invention provides an energy efficient, economical method for dissolving urea, and other endothermic materials, e.g. potassium chloride, ammonium nitrate, sodium chlorate etc., in water, without the use of fossil fuel-derived heat, which comprises: forming a slurry of such material and water, said slurry including said material as both a dissolved and solid phase; and contacting said slurry, as droplets, in direct heat exchange relationship, with a moisture-containing air stream having a temperature greater than the temperature of said droplets of slurry, at conditions whereby both heat and moisture are removed from said moisture-containing air to thereby dissolve at least a portion of said solid phase. This method is especially useful for forming aqueous urea solutions, useful in agricultural applications and having from 19 to 23 percent, by weight, nitrogen. In a method, for dissolving urea in water, in accordance with the present invention, a slurry comprising urea, as both the solid and dissolved phase, in an amount sufficient to yield a solution comprising from 19 to 23 percent, by weight, nitrogen, at a temperature of from about 36° to 64° F., is sprayed, as droplets, downwardly through an upwardly moving moisture-containing air stream, having a temperature of at least about 50° F. preferably from about 70° to 100° F. and a relative humidity of at least about 40 percent, preferably from about 70 to 100 percent, whereby heat and moisture are removed from said moisture-containing air. The sensible heat of the air and the heat derived by the condensation of moisture as well as the condensed moisture, itself, act to dissolve at least a portion of said solid urea phase.

BRIEF DESCRIPTION OF THE DRAWING FIGURE

The invention will be more readily understood by reference to the drawing figure wherein a schematic diagram illustrating the process and apparatus of the instant invention is shown.

DETAILED DESCRIPTION OF THE INSTANT INVENTION

Referring now to the figure of the drawing, a tilting platform shown generally at 10 is positioned contiguous to a screw conveyor-hopper unit 30 which feeds into mixing tank 40. Atop mixing tank 40 is positioned spray box 70.

In operation a truck trailer 11 is positioned on tilting platform 10 with its discharge end 13 adjacent to screw conveyor-hopper unit 30, as shown. Tilting platform 10 comprises a hinged end 15, adjacent screw conveyor-hopper unit 30. At the opposite end of tilting platform 10 a jack or hoist 17 is positioned and adapted to raise lifting end 18 of tilting platform 10. Tilting platform 10 also includes a block 19 against which the rear wheels 21 of trailer 11 are placed. Thus, when the platform is raised by action of jack 17, trailer 11 is tilted and the endothermic material contained therein may slide through open door (not shown) at the discharge end 13 of the trailer. Screw conveyor-hopper unit 30 includes a hopper 31 which is open at one side to enable the discharge end of trailer 11 to discharge into said hopper. A rising screw conveyor 33 is placed with one end 35 in the hopper and a second end 37 feeding into pipe 39 which discharges into mixing tank 40. Thus, endothermic material discharged into the hopper may be conveyed from within the hopper to discharge pipe 39 and ultimately into mixing tank 40. Screw conveyor 33 as shown is fitted with a rotatable screw element 41.

The endothermic material from the hopper is discharged into mixing tank 40 through discharge pipe 39. As shown, mixing tank 40 has upwardly slanted sides and a process water feed pipe 55 which passes through the slanted walls of mixing tank 40 and through which the process water may be fed by a pump (not shown). Mixing tank 40 also has a discharge pipe 57, providing an outlet at the bottom of mixing tank 40, for discharging the slurry of the endothermic material and water formed in mixing tank 40 therefrom. The mixing tank 40 is shaped so that the solid endothermic material tumbles down the slanted sides directly to the discharge pipe 57. Through this discharge pipe, by means of pump 59, is removed a slurry comprising a solution of said endothermic material and a solid phase comprising said endothermic material. As shown, the inlet of the process water feed pipe and the outlet of the slurry discharge pipe are in proximate relationship, whereby the incoming process water is substantially immediately removed from mixing tank 40 for turbulent mixing with the solid endothermic material. The rates of pumping the feed water and the slurry and the rate of feeding the solid endothermic material are regulated to ensure that the incoming process water and the solid endothermic material are substantially immediately removed from the mixing tank 40. The solid endothermic material and the incoming process water are slurried by pumping upward through pipe 61 to overhead spray pipe 63. During the passage through pipe 61 and overhead spray pipe 63 the above discussed turbulent mixing occurs.

In continuous operation, the solution containing the endothermic material, free of the solid phase, is removed through a solution discharge pipe 53 by means of pump 54. The outlet of solution discharge pipe 53 is preferably spaced laterally from and above the outlet of the process water feed pipe and the inlet of the slurry discharge pipe; thus, the solids-free solution may be continuously removed from the mixing tank without dilution by the incoming process water.

Overhead spray pipe 63 includes one or more orifices which can be oriented to either spray the slurry downwardly as droplets or upwardly and allow the droplets to free-fall back into mixing tank. Surrounding said overhead spray pipe 63 is spray box 70 which like mixing tank 40 is rectangular in cross section with the sides thereof registering with the sides of mixing tank 40. As shown, spray box 70 is supported by corner supports 72 which support both mixing tank 40 and spray box 70.

Spray box 70 is enclosed on all sides and the top, with only the bottom being open for the passage of the droplets back into the mixing tank. The bottom is fitted with a mesh or screen 78 for supporting the packing within spray box 70. (The packing is not shown for easier illustration of the apparatus.) A fan opening (not shown) is provided in the roof 73 of spray box 70. The fan 75, positioned adjacent the fan opening, is operable to draw ambient air upwardly through the downwardly descending droplets of slurry. Within spray box 70 is also a demister 77 which is above overhead spray pipe 63 and prevents the escape of the slurry droplets through the fan opening. The demister may conveniently be a porous metal or plastic sheet.

In operation then, a truck may be used to position trailer 11 on tilting platform 10. By operation of the jack 17, the platform may be tilted to enable endothermic material contained in the truck to spill into hopper 31 for conveying by screw conveyor 33 into mixing tank 40. Water is continuously charged into mixing tank 40 through feed pipe 55 and is mixed with the solid endothermic material to form the desired slurry.

The slurry is continuously removed through discharge pipe 57 and by the turbulent mixing obtained as the slurry is pumped through pipe 61 to the overhead spray pipe, a major portion of the solid endothermic material is dissolved and the temperature of the slurry falls. (The slurry may comprise a saturated solution of the endothermic material or the solution may be unsaturated at the temperature obtained by the slurry in pipe 61 and/or overhead spray pipe 63.) The thus cooled slurry is sprayed as droplets downwardly from spray pipe 63 through an upwardly ascending ambient air stream drawn by fan 75. The droplets are of high surface area and thus efficiently heated by contacting, in direct heat exchange relationship, the upwardly ascending air stream. Moreover, moisture from such air stream condenses onto the droplets to provide further water and heat. The combination of heat and additional water, provided by condensing moisture vapor from the air, dissolves additional solid endothermic material in the droplets and thus as the droplets pass downwardly through the packing and fall into mixing tank 40 more endothermic material has been put into solution. The temperature of the downwardly descending droplets may remain the same or be slightly heated by the air stream since, by the mechanism of the method of the instant invention, the heat gained by condensing moisture vapor from the air and by heat exchange with the upwardly ascending air may be balanced by the heat required to dissolve additional solid phase. However in efficient operation the air exiting the fan will be at a lower temperature than the air being drawn through spray box 70. In any event, this air will have a reduced moisture content as compared to the air being drawn into spray box 70 for heat exchange with the downwardly descending droplets. A concentrated solution of said endothermic material, free from solids, may be removed from solution discharge pipe 53, generally at a temperature at or near the crystallization temperature of the solution.

The method of the instant invention achieves maximum thermal efficiency by providing a zone of concentrated solids loading which permits continuous operation at or near the crystallization temperature of the liquid product produced. It is believed that this is accomplished by providing three process zones in the claimed apparatus:

Zone I Solids Dissolution
Zone II Solution Heating
Zone III Solution Separation

In Zone I a relatively high-solids slurry comprising, as a minor portion, recycled slurry, and the slurry formed from the incoming process water and endothermic material, is vigorously mixed to rapidly lower the temperature thereof to below the crystallization temperature while dissolving a major portion of the solid endothermic material fed to the apparatus. Zone I comprises a small volume; however, the ability to provide this high rate of dissolution, in a small volume, is provided by the intense mixing and a high solids to liquid loading provided by pumping the high-solids slurry through pipe 61 and overhead spray pipe 63. The turbulence, that develops as the high-solids slurry is pumped directly through pipe 61 and the overhead spray pipe and is formed into droplets by passage through the orifice[s] of said spray pipe, provides a homogeneous slurry, without additional mechanical mixing, even though the temperature of the slurry is below the crystallization temperature. Moreover as the high-solids slurry passes through Zone I, the solid phase continuously dissolves, thereby lowering the temperature of the slurry and approaching or reaching the saturation point.

In Zone II, droplets of the concentrated slurry, having a temperature below the crystallization temperature, are subjected to direct air heating. As the temperature is raised to near or slightly above the crystallization temperature, for the given solution concentration, a major portion of, if not all of the solid endothermic material not dissolved in Zone I, is dissolved into the liquid phase.

In Zone III, a concentrated solution, at or near crystallization temperature, is removed from the mixing tank and the remaining solids settle to the bottom of the mixing tank and are returned to Zone I as the recycled slurry.

This process thus provides a means to operate at the lowest possible liquid temperatures, the widest possible air to solution temperature, and the highest possible production rate.

A preferred method of operating the process of the instant invention is as follows:

To obtain a solution, comprising 19 to 23 percent nitrogen and having a temperature above the crystallization point of urea, air at a temperature of at least 70° F. and a humidity of at least 70% may be contacted with the downwardly descending droplets of a slurry comprising urea as a solid and in solution. The amount of urea in the slurry is sufficient to provide, upon complete dissolution, a solution having the above concentration of dissolved nitrogen. The rate of flow of the air and the urea-containing slurry is adjusted so that the air exiting spray box 70 is at a temperature of less than about 50° F. and has a relative humidity of less than about 50%. The other process parameters are adjusted to ensure that the urea is substantially completely dissolved in one pass through the apparatus of the instant invention.

The invention is further illustrated by the following examples which are illustrative of a specific mode of practicing the invention and are not intended as limiting the scope of the appended claims.

EXAMPLE 1

Forty six thousand pounds of urea are discharged into mixing tank 40 at a rate of 920 pounds per minute. The feed water flow rate to mixing tank 40 is adjusted to 1193 pounds per minute (143 gallons per minute) at a temperature of 70° F. The product is withdrawn at a rate of 2,113 lbs/min. and at a temperature of 70° F. The upwardly ascending ambient air is pulled through spray box 70 at a flow rate of 53,187 cubic feet per minute, a temperature of 75° F., and a relative humidity of 70%. The slurry is recirculated through pipe 61 at the rate of approximately 7,600 pounds per minute. The amount of water and solid urea is chosen to provide a solution comprising 20% nitrogen. At steady state operation it is found that the temperature of the slurry as it passes through pipe 61 (Zone I) is 43° F.

EXAMPLE 2

In this example, potassium chloride is dissolved in water to provide a solution comprising 14.3% by weight potassium as $K_2O$. The same feed water temperature and ambient air is used in this example as in Example 1. The slurry recirculation rate through pipe 61 is also the same as in Example 1. The feed of potassium chloride is 920 pounds per minute into mixing tank 40 with a water flow rate of 2,944 pounds per minute (353 gallons per minute). Product is withdrawn at a rate of 3871 pounds per minute. The air flow rate is adjusted to provide an excess of heat to the downwardly descending droplets of potassium chloride slurry. In operation it is found that the temperature in Zone I is 50° F. Again, the dissolution of potassium chloride, like urea, is efficiently carried out without the use of fossil fuel-derived heat.

EXAMPLE 3

40,000 lb/hr of dry urea is fed into mixing tank 40 and a 45 percent by weight urea solution, at 50° F., is continuously withdrawn. The process feed water is at a temperature of 70° F. The relative humidity and the flow rate of air, at 75° F., is varied to determine the humidity and air flow rate requirements for efficient operation. The air rates and the moisture condensed from the air are tabulated below for air having a varying relative humidity.

| Percent Relative Humidity | Air, Dry Basis lb/hr | Wet Air ft$^3$/min | Water Condensing lb/hr |
|---|---|---|---|
| 2.2 | Infinite | Infinite | (Infinite Evaporation) |
| 5 | 3,328,000 | 748,400 | (−11,280 Evaporation) |
| 10 | 1,191,000 | 268,200 | (−2,950 Evaporation) |
| 25 | 406,000 | 91,830 | 114 |
| 50 | 194,000 | 44,190 | 956 |
| 100 | 93,400 | 21,600 | 1,356 |

The economic lower limit for operating the process of the instant invention would be between 10 percent and 25 percent relative humidity. That is, at 10 percent relative humidity and below, there is no condensation of moisture to provide heat to the slurry. Note that at a relative humidity of 50 percent, or more, the process of the instant invention is most efficient, i.e. the required airflow rate is reduced more than 50 percent, as the relative humidity increases from 25 to 50 percent, and more than another 50 percent as the relative humidity increases from 50 to 100 percent. For many conditions there is a minimum relative humidity below which the method of the instant invention is inefficient. (For the above conditions at below 2.2 percent relative humidity the invention is inoperable.) For practical purposes, the minimum relative humidity will be higher than this absolute theoretical minimum.

While particular embodiments of the invention have been described, it will be understood of course that the invention is not limited thereto since many obvious modifications can be made and it is intended to include within this invention any such modifications as will fall within the scope of the appended claims. For example, it will be appreciated by those skilled in the art in that the ambient air can be passed through spray box 70 in a cross direction as well as upwardly. Moreover, as discussed above, the droplets may be sprayed upwardly or downwardly and in either event they will free fall through the spraybox back to the mixing tank. Moreover, it will be understood that the apparatus described above can be operated on a continuous or a batch basis.

Having now described the invention, what it claimed is:

1. An apparatus for dissolving endothermic materials, without fossil fuel-derived heat, which comprises:

(a) a mixing tank, means for introducing endothermic material, as a solid phase, into said mixing tank, a process water feed pipe connected to said mixing tank for feeding process water into said mixing tank for forming a slurry of the endotheric material and the process water, and a slurry discharge pipe connected to said mixing tank for removing the slurry from said mixing tank, (b) an orificed spray pipe, in fluid communication with said slurry discharge pipe, said orificed spray pipe being positioned above said mixing tank and arranged so as to spray droplets of the slurry downwardly into said mixing tank, and (c) a spray box enclosing said spray pipe, and having an open bottom to thereby allow the spray droplets to descend into said mixing tank, said spray box further having an opening for air and a fan in flow communication with said opening for drawing ambient air throught the spray box for direct heat exchange with the spray droplets.

2. The apparatus of claim 1 wherein said spray box has a foof including said opening and said fan is positioned above said opening to draw ambient air upwardly through said downwardly descending spray droplets.

3. The apparatus of claim 2 wherein said spray box has a mesh or screen bottom for supporting a packing.

4. The apparatus of claim 3 further including screw conveyor-hopper means for storing and conveying endothermic material to said means for introducing endothermic mterial.

5. The apparatus of claim 4 further including a tilting platform for feeding endothermic material directly from a trailer into said screw conveyor-hopper means, said tilting platform being hinged at an end proximate said screw conveyor-hopper means, and having a distal end adapted to be raised by a jack to thereby tip a trailer positioned on said tilting platform whereby endothemic material contained in the trailer may be spilled directly into said screw conveyor-hopper means.

6. The apparatus of claim 2 wherein said mixing tank includes a solution discharge pipe for continuous removal of a solids-free solution from said mixing tank.

7. The apparatus of claim 6 wherein said solution discharge pipe has an outlet which is space laterally from and above an outlet of said process water feed pipe and an outlet of said slurry discharge pipe.

8. The apparatus of claim 2 wherein said process water feed pipe has a discharge outlet in proximate relationship to an inlet of said slurry discharge pipe.

9. The appartus of claim 1 whereinsaid mixing tank has slanted sides and said means for introducing endothermic material is located above an inlet of said slurry discharge pipe.

* * * * *